United States Patent [19]

Butselaar et al.

[11] Patent Number: 5,118,340
[45] Date of Patent: Jun. 2, 1992

[54] PROCESS FOR THINNING OF STONE FRUIT BLOSSOMS USING ALKOXYLATED AMINES

[75] Inventors: Robert J. Butselaar, Hilversum, Netherlands; Frits W. R. Gonggrijp, Bryanston, South Africa

[73] Assignee: Akzo NV, Arnhem, Netherlands

[21] Appl. No.: 718,714

[22] Filed: Jun. 21, 1991

[30] Foreign Application Priority Data

Jun. 26, 1990 [EP] European Pat. Off. ........ 90201685.6

[51] Int. Cl.⁵ ...................... A01N 33/04; A01N 33/12
[52] U.S. Cl. ......................................... 71/121
[58] Field of Search .......................................... 71/121

[56] References Cited

FOREIGN PATENT DOCUMENTS 0257686 3/1988 European Pat. Off.

OTHER PUBLICATIONS

Byers et al., "Flower Bud Removal with Surfactants for Peach Thinning", *Hortscience*, 17:377-378, 1982.
Byers et al., CAS 100:63393j, "Chemical Peach Thinning with Surfactants and Ammonium Nitrate", (*J. Hortic. Sci.*, 58:517-19) 1984.
Byers et al., "Peach Flower Thinning . . . ", *J. Amer. Soc. Hort. Sci.*, 110:662-667, 1985.
Tom Arthur, *Fertilize Your Blooms Off*, Apr. 1987, p. 9, 74.
A. D. Webster & Linda Andrews, Fruit Thinning Victoria Plums (*Prunus domestica* L.): Preliminary Studies with Paclobutrazol, 1985, pp. 193-199.
A. Blanco, Fruit Thinning of Peach Trees (*Prunus persica* (L.) Batsch.): *The Effect of Paclobutrazol on Fruit Drop and Shoot Growth*, 1987, pp. 147-155.
R. E. Byers, C. G. Lyons, Jr. & S. J. Donohue, *Effect of Chemical Deposits from Spraying Adjacent Rows on Efficacy of Peach Bloom Thinners*, 1985, pp. 1076-1078.
H. Vijverberg, *Chemische Vruchtdunning* 1985, pp. 494-495.
H. Peerbooms, *Uit Het Fruitteelt-Kundig Onderzoek*, 1983, pp. 418-419.
J. D. Stadler, C.3 *Uitdun Van Steenvrugte*, 1975, pp. 1-4.
S. Zilkah, I. Klein & I. David, *Thinning Peaches and Nectarines with Urea*, 1988, pp. 209-216.
C. E. Gambrell, Jr., D. C. Coston & E. T. Sims, Jr., *Results of Eight Years with CGA-15281 as a Postbloom Thinner for Peaches*, 1983, pp. 605-608.

*Primary Examiner*—Richard L. Raymond
*Assistant Examiner*—S. Mark Clardy
*Attorney, Agent, or Firm*—Louis A. Morris; David H. Vickrey

[57] ABSTRACT

A process for thinning stone fruit blossoms is disclosed. In the process, a compound selected from certain alkoxylated amines and alkoxylated quaternary ammonium compounds is applied to stone fruit trees at some point after 50% blossom to thereby reduce the number of blossoms on the stone fruit tree. In this manner, the amount of fruit thinning which must be done by hand can be substantially reduced without decreasing the quantity of marketable fruit produced by an orchard or harming the trees or the workers in the orchard.

10 Claims, No Drawings

PROCESS FOR THINNING OF STONE FRUIT BLOSSOMS USING ALKOXYLATED AMINES

The present application for patent is entitled to the benefit of an earlier filing date in a foreign country under 35 U.S.C. 119, based on priority application Serial No. EP90201685.6, June 26, 1990, which is hereby incorporated by reference.

BACKGROUND OF THE INVENTION

The practice of fruit thinning in stone fruit is a standard management procedure for the deciduous fruit industry. Fruit thinning is necessary since stone fruit trees tend to produce far too many blossoms each year. The excess of blossoms leads to a large quantity of fruit which is often too small to be marketable. Further, when the fruit density is too great on portions of the fruit trees, the weight of the fruit may become too large to be supported by the tree and the entire branch, including its fruit, may be lost.

Thus, the general object of chemical blossom thinning is to reduce the number of viable blossoms on a stone fruit tree during the blossom period to thereby provide a tree having a lower fruit density thereon. In this manner, overloading of sections of the tree can be avoided and larger fruit can be produced since the same amount of sustenance will be supplied to a smaller number of viable fruit.

In practice, fruit thinning is generally done by hand. In other words, workers must go to each tree and remove sufficient fruit to provide satisfactory fruit thinning. Apart from being a time consuming and labor intensive exercise, fruit thinning by hand is often very expensive.

There exist various chemicals which are currently used in the industry for blossom thinning purposes. These existing products are generally toxic to both the surrounding environment as well as the operators that are charged with the task of applying these chemical agents. Furthermore, many of the existing products are also phytotoxic to the orchard. For the above reasons, chemical blossom thinning in stone fruit has not yet become a widely used procedure.

A summary of fruit thinning methods can be found in "C.3 Uitdun Van Steenvrugte", Stadler, J. D., Navorsingsinstituut vir Vrugte en Vrugtetegnologie, Stellenbosch, South Africa, 1975. In this article both the hand thinning and chemical thinning of stone fruit are discussed. As a chemical thinning agent is disclosed DNBP (Gebutox ™ 50% from Hoechst). It is further disclosed that this agent effectively reduces the number of blossoms on stone fruit trees and leads to increased fruit size. However, the agent has been found to be phytotoxic to the fruit trees and other plants as well. Further, the application of this agent poses some risk to the person applying it.

Another agent which has been used for fruit thinning is Paraquat ®. However, this agent has been found to be toxic to humans and to cause damage to the crop treated as well as other surrounding plants. Both DNBP and Paraquat ® are now withdrawn from government approval in many countries for use in blossom thinning of stone fruit for reasons of toxicological concern and orchard safety.

Accordingly, there exists a need in the stone fruit industry for a chemical blossom thinning agent which exhibits a relatively low phytotoxicity, is not harmful to humans applying the agent and is capable of providing acceptable results in blossom thinning and the subsequently required fruit thinning effect. These and other objects of the present invention will be apparent from the summary and detailed description which follow.

SUMMARY OF THE INVENTION

The present invention relates to a process for thinning of stone fruits which comprises the step of applying to at least one stone fruit bearing tree after at least 50% blossom, an effective amount of at least one compound selected from the group consisting of alkoxylated amines represented by the following general formula:

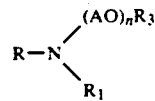

wherein n is an integer from 1 to 50, A represents an alkylene group and when n>1, each A may be the same or different alkylene groups, R is selected from straight or branched chain alkyl or alkenyl groups having 8 to 22 carbon atoms and groups represented by the formula:

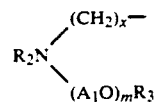

wherein m is an integer from 1-50, $A_1$ represents an alkylene group and when m>1, each A1 may be the same or different alkylene groups, x is an integer from 1-6, and $R_2$ is independently selected from the same groups as R, $R_3$ is selected from hydrogen, 1-8 carbon atom straight or branched chain alkyl and alkenyl groups and aryl groups having up to 8 carbon atoms; and R1 is selected from hydrogen, straight or branched chain alkyl and alkenyl groups having 1-22 carbon atoms, a group represented by the formula:

$$(A_2O)_{n'}R_3$$

wherein n' is an integer from 1 to 50 and $A_2$ represents an alkylene group and when n'>1 each $A_2$ may be the same or different alkylene groups; and alkoxylated quaternary ammonium compounds represented by the following general formula:

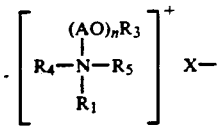

wherein n, A, $R_1$ and $R_3$ are as defined above, X is an anion, $R_5$ is selected from hydrogen, straight or branched chain alkyl or alkenyl groups having 1 to 4 carbon atoms, benzyl or $R_5X-$ can be carboxymethyl as in betaines and oxygen as in amine oxides; $R_4$ is selected from straight or branched chain alkyl and alkenyl groups having 8-22 carbon atoms and groups represented by the formula:

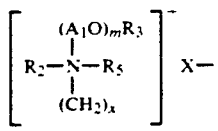

wherein $A_1$, m, $R_2$, $R_3$, $R_4$, $R_5$ and x are as defined above; to reduce the number of fruit-producing blossoms on the stone fruit tree.

More particularly X may be halides such as Cl— and Br—, or sulfates such as $CH_3SO_4$— and $C_2H_5SO_4$—, among others. The anion associated with these quaternary ammonium compounds is not critical to the process of the present invention.

Several of the foregoing compounds are known from our previous European Patent Application 0 257 686 published on 2 March 1988 which discloses several alkoxylated amines and their use as activity promoting additives for herbicides and fungicides. This published patent application also discloses a method for making these compounds. The disclosure of this patent is hereby incorporated by reference.

DETAILED DESCRIPTION OF THE INVENTION

As a result of extensive research it has now been found that the above-identified compounds can be used as chemical blossom thinning agents for stone fruit. These compounds all exhibit a substantial blossom thinning effect and human toxicity and phytotoxicity studies have shown the compounds to have acceptably low levels of toxicity to humans and other plants. Further, the compounds do not cause significant harm to useful insect populations and thus are advantageous in this respect as well.

The amino compounds of the present invention may be prepared by reacting an amine selected from the group consisting of R—$NH_2$, RRNH, and R—N-H—$((CH_2)_x$—NH$)_n$—R' wherein R and R' are aliphatic hydrocarbon groups having 8-22 carbon atoms, n=1-5 and x is an integer from 1-6; with at least one alkylene oxide.

The preferred alkylene oxides for use in the present invention are ethylene oxide, propylene oxide, isobutylene oxide and butylene oxide. The compounds of the present invention are made in such a way as to introduce varying numbers of alkylene oxide units onto the amino nitrogen. Thus, these alkylene oxide groups may be all the same, such as, for example, one or more ethylene oxide units, or the groups may be different to form, for example, block copolymer chains of ethylene oxide and propylene oxide units, random copolymer chains consisting of several units of each of two or more different alkylene oxides, or alternating units of two or more alkylene oxides. Any conceivable combination of alkylene oxide units up to 50 units long may be employed at each location on the amino nitrogen which is to contain such units. In addition, a single amino nitrogen may contain two different alkylene oxide chains attached thereto or two chains which are the same.

In the most preferred embodiments of the present invention, block copolymer chains of ethylene oxide and one or more of propylene oxide or butylene oxide are employed. Preferably, the molar weight of the compounds used in the present invention is less than 8000 though higher molecular weight compounds can be employed in some circumstances.

The amino compounds can also be quaternized by known quaternization methods to produce quaternary ammonium compounds which are also useful in the process of the present invention. The fourth substituent added to the amino nitrogen by quaternization may be an alkyl, aryl or alkenyl group having 1 to 4 carbon atoms. The anion associated with such quaternary ammonium compounds is not critical to the process of the present invention.

Typical compounds suitable for use in the process of the present invention include, but are not limited to, cocobis (2-hydroxyethyl)methylammonium chloride, polyoxyethylene (15) cocomethylammonium chloride, oleylbis (2-hydroxyethyl)methylammonium chloride, polyoxyethylene (15) stearylmethylammonium chloride, cocobis (2-hydroxyethyl)amine, polyoxyethylene(5)cocoamine, polyoxyethylene(15)cocoamine, tallowbis (2-hydroxyethyl)amine, polyoxyethylene(5)tallowamine, polyoxyethylene(15)tallowamine, tallow/oleylbis(2-hydroxyethyl)amine, oleylbis(2-hydroxyethyl)amine, polyoxyethylene(5)oleylamine, polyoxyethylene(15)oleylamine, hydrogenated tallowbis(2-hydroxyethyl)amine, hydrogenated polyoxyethylene(5)tallowamine, hydrogenated polyoxyethylene(15)tallowamine, hydrogenated polyoxyethylene(50)tallowamine, N,N',N'-tris(2-hydroxyethyl)-N-tallow-1,3-diaminopropane, N,N',N'-polyoxyethylene(10)-N-tallow-1,3-diaminopropane, and N,N',N'-polyoxyethylene(15)-N-tallow-1,3-diaminopropane.

The process of the present invention is useful for blossom thinning of stone fruit to produce a reduced number of larger, more marketable fruit from each tree and at the same time minimize fruit losses due to breaking of tree branches in harsh weather. The present process also provides a method which enables the equivalent amount of control of the position of fruit on a particular tree as the prior art hand thinning method.

The process of the present invention is to be applied to stone fruit trees which have reached at least 50% blossom. 100% blossom is the point in time when all blossoms have just opened. Thus, 50% blossom is the point in time when half of the blossoms on a particular tree have opened. The fruit thinning process can be carried out at any point after 50% blossom and up to one or two weeks after 100% blossom on some stone fruit. The optimum time to thin a stone fruit tree will depend upon several factors including the type of fruit, the cultivar, the climatic conditions and the type and amount of thinning agent being applied. For some fruit or cultivar species, the best thinning effects are accomplished before the trees reach 100% blossom whereas for others it is best to wait until several days after 100% blossom has been reached.

The process of the present invention is carried out by the application of an effective amount of at least one compound as defined herein to stone fruit trees to thereby produce a reduction in the number of blossoms and consequently produce a reduction in the number of fruit, as well as an increase in the size of the fruit produced. The compounds are preferably applied in the form of an aqueous solution in a concentration of 0.25 to 10% and more preferably from 0.5 to 5%. The lower limit is generally determined by the upper limit on application volume for the particular application equipment being employed, as well as by the type of stone fruit being thinned and the particular compound used.

The upper concentration limit will generally be dictated by phytotoxicity considerations as higher concentrations of certain compounds have a localized phytotoxic effect on the trees. Thus, a concentration should be selected which provides adequate fruit thinning without unwanted phytotoxic effects on the remainder of the tree. The attached examples show that such concentrations can be selected by routine experimentation with the particular species of stone fruit to be thinned.

The composition is preferably applied in a manner similar to the manner in which commercial insecticides are applied. More particularly, conventional equipment such as knapsack sprayers, hand held spray guns, mist blowers, and aerial spraying equipment among others may be used. The composition is applied the same way as in pesticide application.

The process of the present invention has the significant advantages that it thins blossoms to the extent that hand fruit thinning can be eliminated or considerably reduced. it can be done in a manner which is safe for the crops and the treatment has no long term phytotoxic effect on the orchards, if carried out correctly. The compounds will not harm beneficial insects when applied within the normal application volume, and the process appears to be environmentally acceptable, non-hazardous to operators of the application equipment, and noncorrosive to the equipment.

The present invention will be further illustrated by the examples appended hereto.

EXAMPLES 1-4

Materials and Methods

The treatments of the four fields trials have all been applied by motor driven piston pump equipment fitted with hand held spray lances. Operating pressure are kept at a constant two Bars. For spray volumes applied see the following table.

TABLE I

| Example No. | Fruit/Cultivar | Locality | Spray volume applied Liter per HA |
|---|---|---|---|
| 1 | Plums (Ruby Nel) | Franschhoek | 3350 l |
| 2 | Plums (Harry Pickstone) | Franschhoek | 2020 l |
| 3 | Plums (Ruby Nel) | Grabouw | 2500 l |
| 4 | Peaches (Culembourg) | Paarl | 2750 l |

The variable volume of carrier used can be ascribed to the variation in tree size between the various experimental sites, and variation in blossom density between the different cultivars.

The four trials were designed as randomized block experiments with varying numbers of replicates (10-12 replicates). The modified fatty amine used in these experiments was an Akzo development product under the name and code number: Armoblen ® ACER 89002. Armoblen ® ACER 89002 can be represented by the general formula:

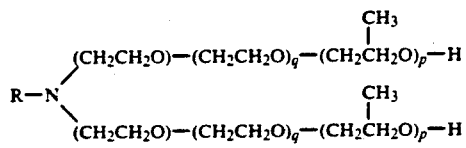

wherein $p=12$, $q=4$ and R is a hydrocarbon group derived from tallow fatty acid. Concentrations used varied from 0%-5% (volume/volume). As far as timing of the applications were concerned, this was done as close as possible to the 100% blossom stage (for plums). In peaches all treatments except treatment no. 3 (see table No.V), were also applied at full blossom, with treatment no. 3 at full blossom plus two days. An initial assessment was carried out just after fruit set. The method of initial assessment was to weigh the fruit which still remained to be hand thinned in order to achieve the optimal yield/fruit size ratio and tree frame distribution. In other words the lower the weight of fruit which remained to be hand-thinned the stronger the chemical blossom thinning effect that had been achieved. Final assessments were carried out at harvest.

Results

The following examples (tables II-V) give the results obtained in the four field trials conducted.

EXAMPLE 1

Plums (Ruby Nel)

TABLE II

| Treatments | Concentration (volume/volume) | Mean fruit weight as thinned by hand (kg*) |
|---|---|---|
| 1. Control | — | 12.6 |
| 2. Armoblen ® ACER-89002 | 1% | 11.4 |
| 3. Armoblen ® ACER-89002 | 2% | 9.0 |
| 4. Armoblen ® ACER-89002 | 3% | 6.0 |
| 5. Armoblen ® ACER-89002 | 4% | 5.6 |
| 6. Armoblen ® ACER-89002 | 5% | 2.5 |

*mean weight of 12 replicates

It is clear from this table that all treatments with Armoblen ® ACER-89002 produced fruit thinning effects. The best results were obtained by 1-3% Armoblen ® ACER-89002 for this particular cultivar and dosages of 4-5% produced slight overthinning.

Hand-thinning is always necessary for obtaining optimal tree frame distribution and thus, the mean fruit weight as thinned by hand is not completely indicative of an optimum thinning effect.

EXAMPLE 2

Plums (Harry Pickstone)

TABLE III

| Treatments | Concentration (volume/volume) | Mean fruit weight as thinned by hand (kg*) |
|---|---|---|
| 1. Control | — | 18.1 |
| 2. Armoblen ® ACER-89002 | 1% | 14.7 |
| 3. Armoblen ® ACER-89002 | 2% | 16.0 |
| 4. Armoblen ® ACER-89002 | 3% | 13.5 |
| 5. Armoblen ® ACER-89002 | 4% | 9.8 |
| 6. Armoblen ® ACER-89002 | 5% | 3.8 |

*mean weight of 10 replicates

In this trial all treatments with Armoblen ® ACER 89002 produced fruit thinning. The 3% treatment produced the optimum result.

EXAMPLE 3

Plums (Ruby Nel)

TABLE IV

| Treatments | Concentration (volume/volume) | Mean fruit weight harvested (kg*) |
|---|---|---|
| 1. Control | — | 236 |
| 2. Armoblen ® ACER-89002 | 1% | 143.2 |

TABLE IV-continued

| Treatments | Concentration (volume/volume) | Mean fruit weight harvested (kg*) |
|---|---|---|
| 3. Armoblen ® ACER-89002 | 2% | 88.5 |
| 4. Armoblen ® ACER-89002 | 3% | 36.0 |
| 5. Armoblen ® ACER-89002 | 4% | 28.2 |
| 6. Armoblen ® ACER-89002 | 5% | 19.5 |

*Mean weight of 6 replicates

In this trial where control trees had not been hand thinned after fruit set the 1% Armoblen ® ACER-89002 treatment gave an optimal fruit size:weight ratio with the 2% treatment giving an acceptable result. Concentrations over 2% resulted in overthinning.

The treatments in this experiment were applied under extremely high temperature conditions (>30° C.).

EXAMPLE 4

Peaches (Culembourg)

TABLE V

| Treatments | Concentration (volume/volume) | Mean fruit weight as thinned by hand (kg*) |
|---|---|---|
| 1. Control | — | 6.2** |
| 2. Armoblen ® ACER-89002 | 1% | 13.9 |
| 3. Armoblen ® ACER-89002 | 2% | 13.0*** |
| 4. Armoblen ® ACER-89002 | 2% | 11.4 |
| 5. Armoblen ® ACER-89002 | 3% | 10.0 |
| 6. Armoblen ® ACER-89002 | 4% | 6.6 |

*mean weight of 10 replicates
**Blossom of the Control trees was hand-thinned the same day as the chemical treatments were applied
***Treatment applied at full Blossom plus two days In this peach blossom thinning trial the 4% Armoblen ® ACER-89002 treatment gave as good a result as the hand-thinned Control, Control trees were hand-thinned at full blossom. Where Armoblen ® ACER-89002 is applied for the purpose of Peach blossom thinning, the optimum timing of such an application does not coincide with the full blossom stage as with plums. In plums, as the previous series of experiments indicated, the optimum application time lays around full blossom. There are however indications, that treatments commenced at the 70-80% blossom stage achieve acceptable results at reduced concentrations of Armoblen ® ACER 89002.

EXAMPLE 5

Phytotoxicity

In plums the first flush of leaves following the full blossom application showed a very slight leaf tip scorch, accompanied by temporary slight bronzing. Those leaves developed normally in colour and size with symptoms disappearing in a relatively short time span (7-10 days). No abnormal leaf drop was recorded. Subsequent foliar development did not show any of the symptoms of phytotoxicity. The above observed symptoms only occurred at the higher concentrations (>4%). Identical symptoms were observed in the Peach experiment. These symptoms occurred at dose rates from 3% upwards. Symptoms disappeared totally as from two weeks after application. Treated trees have been observed for three seasons with no noticeable chronic phytotoxic effects. Fruit set, fruit development, leaf, twig, branch formation and budding were normal.

EXAMPLE 6

Nectarines

Variety: Sunlite
Locality: D. Malan, Solomonsvlei, Drakenstein South, Paarl

TABLE VI

| Treatments | Concentration (volume/volume) | Mean Weight - (kg) Fruit per tree Thinned |
|---|---|---|
| Armoblen ® ACER-89002 | 1% | 1.110 |
| Armoblen ® ACER-89002 | 2% | 0.883 |
| Armoblen ® ACER-89002 | 3% | 0.724 |
| Armoblen ® ACER-89002 | 4% | 0.528 |
| Armoblen ® ACER-89002 | 5% | 0.555 |

In the untreated part of the orchard and thus unsprayed trees, two manual thinning operations were carried out. Only one thinning was done in the treated plots. Dosage related thinning response obtained with the higher concentrations (4-5%) resulted in excessive fruit thinning and thus no further dosage related response was observed at 5%.

There were signs of variable efficacy between trees with similar concentrations. The less vigorous trees appeared to be more susceptible to treatment and exhibited greater degrees of thinning than the more vigorously growing trees.

EXAMPLES 7 AND 8

The following thinning agents, from Akzo Chemical Division, were sprayed on plums (cv HEV Pickstone) at different stages during bloom: Armoblen ® ACER 89002 at 2, 3 and 4% (v/v); Armoblen ® ACER-89001 at 2 and 6% (v/v); Armoblen ® T25 at 2% (v/v). The thinning effect of these treatments was compared with that of a Paraquat ® spray (0.0025%-v/v) and with a thinning by hand (Table 7). The stages of application were 80% FB (i.e. 80% Full Blossom) and (FB+1 day). At harvest, the fruit were sized and the total yield per tree was determined. The percentage of non-marketable fruit based on the size was used as a criteria for the success of thinning. The following treatments provided similar or better thinning than a hand-thinned standard: Armoblen ® ACER 89002 at 4% applied at either 80% FB or (FB+1 day); Armoblen ® ACER 89001 at 2% applied at 80% FB and Armoblen ® ACER 89001 6% applied at (FB+1 day), Paraquat ® (0.0025%) applied at 80% FB and Armoblen ® T25 (2%) sprayed at 80% FB.

Materials and Methods

Crop: Plums
Cultivar: H.E.V. Pickstone
Locality: de Rust, Grabouw
Spacing: Between Rows: 4.5 m
Spacing Between Trees: 2.5 m
Date of Full Bloom: 09/09/87
Method of Application: Knapsack Sprayer with hollow cone nozzle.
Volume Spray Mixture/ha: 1500 liter
Dates of Application: 80% of FB: 07/09/87 Full Bloom: 09/09/97
Date of Harvest: 25/01/88
Trial Layout: Randomized Treatments
Replicates: 3
Plot Size: Single Tree

TABLE VII

The effect of Thinning Agents on Thinning of Plums

| Treatments Number | Chemical | Conc. % w/w | Timing | Undersize % <43 mm | Yield Tons/ha | Saleable Tons/ha | % Saleable Tons/ha |
|---|---|---|---|---|---|---|---|
| 1 | Control | | | 50.2 | 54.3 | 27 | 49.7 |
| 2 | Armoblen ® ACER-89002 | 2 | 80% FB | 36.5 | 46.5 | 29.5 | 63.4 |
| 3 | Armoblen ® ACER-89002 | 3 | FB+1 | 31.9 | 44.7 | 30.4 | 68.0 |
| 4 | T25 | 2 | FB+1 | 22.6 | 41 | 31.7 | 77.3 |
| 5 | Paraquat ® | .0025 | 80% FB | 18.6 | 34.9 | 28.4 | 81.4 |
| 6 | Armoblen ® ACER-89001 | 2 | 80% FB | 18.5 | 48 | 39.1 | 81.4 |
| 7 | Armoblen ® ACER-89002 | 4 | FB+1 | 12.5 | 39.7 | 34.7 | 87.4 |
| 8 | Armoblen ® ACER-89001 | 6 | FB+1 | 12.4 | 37.9 | 33.2 | 87.5 |
| 9 | Armoblen ® ACER-89002 | 4 | 80% FB | 4.6 | 27.8 | 26.5 | 95.0 |
| 10 | Handthin | | | 21 | 43.4 | 34.3 | 79.0 |

The Armoblen ® ACER-89002 (4%), Armoblen ® ACER-89001 (2%) and Paraquat ® sprayed at 80% FB as well as Armoblen ® ACER-89002 (4%), Armoblen ® ACER-89001 (6%) and Armoblen ® T25 (2%) all sprayed at FB+1, produced yields of marketable sized fruits comparable or better than the yields achieved with hand-thinning.

EXAMPLE 8

The following chemical agents from Akzo were screened on expected blossom thinning effect. All products were applied at 3% (v/v) and their thinning effect rated opposite the Armoblen ® ACER-89002.

Materials and Methods

Crop: Plums

Cultivar: Harry Pickstone
Locality: de Rust, Grabouw
Volume spray mixture/ha: 2500 Liter
Method of application: Motorized Knapsack sprayer
Trial Layout: Randomized Treatments
Replicates: 2
Plot Size: Single Tree
Dates of application: 23/8/89, i.e. full bloom stage, 90-95% open flower.

TABLE VIII

| Treatments number | chemical | concentration % v/v | timing | observation* | thinning | foliar phytotoxicity |
|---|---|---|---|---|---|---|
| 1 | Ethoquad ® C/25 | 3 | FB | 4 | yes | scorch |
| 2 | Armoblen ® KII/1279 | 3 | FB | 4 | yes | no |
| 3 | Armoblen ® KII/1299 | 3 | FB | 4 | yes | no |
| 4 | Armoblen ® ACER-89002 | 3 | FB | 3 | yes | no |

*Rating Scale (0-5)
3 = required flower disintegration
4 = +75% flower abortion
5 = 100% flower abortion The treatments with numbers 1-3 were a bit harsh, but this test demonstrates that, at slightly lower concentrations, these are useful thinning agents.

Ethoquad ® C/25

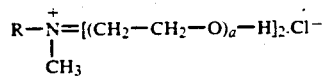

wherein R is a hydrocarbon group derived from Coco fatty acid and a=15.

Armoblen ® K II/1279

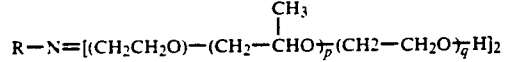

wherein R is a hydrocarbon carbon derived from coco fatty acid, p=12 and q=5.

Armoblen ® K II/1299

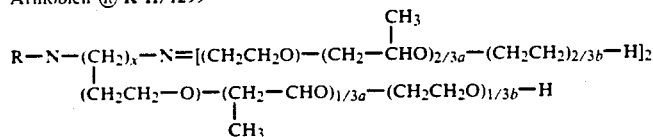

wherein R is a hydrocarbon group derived from tallow fatty acid, a=12, b=5 and x=3.

EXAMPLE 9

| Plums | Remarks |
|---|---|
| Variety: Sungold | -pH spray water adjusted |
| Locality: Western Cape | with a buffer to pH 5 |

TABLE IX

| Treatment[1] 89/09/08 (full blossom stage) | Concentration % w/w and spray volume (Ltr) | Mean No. of fruit counted 0.5 m² as thinned by hand (12 replicates) | Mean Fruit size (diameter in mm) 50 harvested fruit/tree |
|---|---|---|---|
| Control | — | 10.3 + 0.2 (b) | 50.1 (b) |
| Armoblen ® ACER-89002 | 1.5% (2100 Ltr) | 2.4 + 0.1 (a) | 55.0 (a) |
| Armoblen ® ACER-89002 | 1.5% (3100 Ltr) | 2.3 + 0.1 (a) | 56.2 (a) |

[1] Treatments were carried out using standard farmers equipment, i.e. mist. blower.

In the control part of the orchard and thus unsprayed trees, two manual thinning operations were carried out. Only one thinning was done in the treated plots. A statistically significant fruit size diameter (a) vs (b) was found for the treated plots opposite the control plots. This means that an important quality aspect assessment, i.e. fruit size, was significantly improved in the treated plots.

EXAMPLE 10

Plums
Variety: Ruby Nel
Locality: Grabouw

TABLE X

| Treatment 89/08/17 (full blossom stage) | Concentration (% w/w) and spray volume (ltr) | Mean fruit weight as thinned by hand (kg) (10 replicates) |
|---|---|---|
| Control | — | 47.4 + (b) |
| Armoblen ® ACER-89002 | 2% (1664) | 29.6 (a) |
| Armoblen ® ACER-89002 | 3% (1682) | 31.1 (a) |

This trial resulted in an 'ideal' degree of blossom thinning. Treatments resulted in just enough fruit set to correct the hand thin to such a degree that ideal fruit positioning per branch was achieved.

The foregoing examples have been presented for purposes of illustration and description only and are no to be construed as limiting the scope of the invention in any manner. Accordingly, the scope of the invention is to be determined by the claims appended hereto.

What is claimed:

1. A process for thinning of stone fruit blossoms which comprises the step of applying to at least one stone fruit bearing tree after at least 50% blossom, an effective amount of at least one compound selected from the group consisting of alkoxylated amines represented by the following general formula:

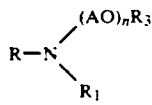

wherein n is an integer from 1 to 50, A represents an alkylene group and when n > 1, each A may be the same or different alkylene groups, R is selected from straight or branched chain alkyl or alkenyl groups having 8 to 22 carbon atoms and groups represented by the formula:

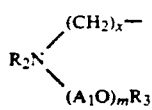

wherein m is an integer from 1-50, $A_1$ represents an alkylene group and when m > 1, each $A_1$ may be the same or different alkylene groups, x is an integer from 1-6, and $R_2$ is independently selected from the same groups as R; $R_1$ is selected from hydrogen, straight or branched chain alkyl and alkenyl groups having 1-22 carbon atoms, a group represented by the formula:

wherein n' is an integer from 1 to 50 and $A_2$ represents an alkylene group, and when n' > 1 each $A_2$ may be the same or different alkylene groups; and each $R_3$ is independently selected from hydrogen, straight or branched chain alkyl and alkenyl groups having 1-8 carbon atoms and aryl groups of up to 8 carbon atoms; and alkoxylated quaternary ammonium compounds represented by the following general formula:

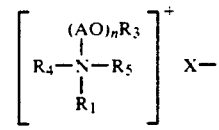

wherein n, $R_1$, A and $R_3$ are as defined above, X— is an anion, $R_5$ is selected from hydrogen, straight or branched chain alkyl and alkenyl groups having 1 to 4 carbon atoms, benzyl or $R_5X$— can be carboxymethyl as in betaines and oxygen as in amine oxides; and $R_4$ is selected from straight or branched chain alkyl groups having 8-22 carbon atoms and groups represented by the formula:

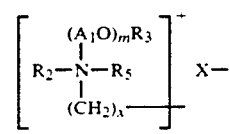

wherein $A_1$, m, $R_2$, $R_3$, $R_5$ and x are as defined above; to reduce the number of fruit-producing blossoms on the stone fruit tree.

2. A process in accordance with claim 1 wherein said compound is applied in the form of an aqueous solution having a concentration of from 0.25 to 10%.

3. A process in accordance with claim 2 wherein said compound has a molecular weight of less than 8000 grams/mole.

4. A process in accordance with claim 3 wherein said compound is an alkoxylated quaternary ammonium compound represented by the general formula:

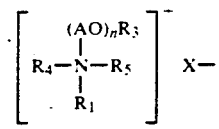

wherein n is an integer from 1 to 50, X— is an anion, A represents an alkylene group and when n > 1, each A may be the same or different alkylene groups, $R_5$ is selected from hydrogen, straight or branched chain alkyl and alkenyl groups having 1–4 carbon atoms, benzyl, or $R_5X$— can be carboxymethyl as in betaines, and oxygen as in amine oxides; $R_4$ is selected from straight or branched chain alkyl or alkenyl groups having 8 to 22 carbon atoms or a group represented by the formula:

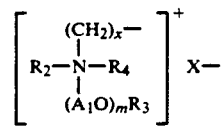

wherein m is an integer from 1 to 50, X— is an anion, $R_5$ is as defined above, $A_1$ represents an alkylene group and when m > 1, each $A_1$ may be the same or different alkylene groups, x is an integer from 1 to 6, $R_2$ is selected from straight or branched chain alkyl or alkenyl groups having 8-22 carbon atoms; and $R_1$ is selected from hydrogen, straight or branched chain alkyl or alkenyl groups having 1 to 22 carbon atoms, a group represented by the formula:

$(A_2O)_{n'}R_3$ wherein n' is an integer from 1 to 50 and $A_2$ represents an alkylene group; when n' > 1 each $A_2$ may be the same or different alkylene groups, and $R_3$ is selected from hydrogen, straight or branched chain alkyl or alkenyl groups having 1 to 8 carbon atoms and aryl groups having up to 8 carbon atoms; to reduce the number of fruit-producing blossoms on the stone fruit tree.

5. A process in accordance with claim 3 wherein said compound is an alkoxylated amine represented by the following general formula:

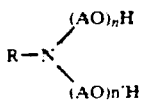

wherein n and n' are integers from 1 to 50, A represents an alkylene group and when n or n' are greater than 1, each A may be the same or different alkylene groups, and R is selected from straight or branched chain alkyl or alkenyl groups having 8 to 22 carbon atoms.

6. A process in accordance with claim 5 wherein n > 1 and A includes both ethoxy groups and propoxy groups.

7. A process in accordance with claim 3 wherein said compound is an alkoxylated amine represented by the following general formula:

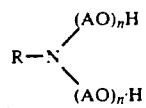

wherein n and n' are integers from 1 to 50. A represents an alkylene group and when n or n' are greater than 1, each A may be the same or different alkylene groups, R is a group represented by the formula:

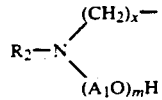

wherein m is an integer from 1 to 50, $A_1$ represents an alkylene group and when m > 1, each $A_1$ may be the same or different alkylene groups; x is an integer from 1 to 6, and $R_2$ is selected from straight or branched chain alkyl or alkenyl groups having 8-22 carbon atoms.

8. A process in accordance with claim 3 wherein R is selected from alkyl groups having 12-22 carbon atoms.

9. A process in accordance with claim 3 wherein said compound is applied as an aqueous solution having a concentration of 0.1 to 5.0% v/v.

10. A process in accordance with claim 3 wherein said compound is an amine oxide represented by the following general formula:

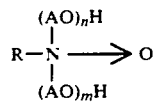

wherein R, A, n and m are as defined in claim 1.

* * * * *